US007664842B2

(12) United States Patent
Tanaka

(10) Patent No.: US 7,664,842 B2
(45) Date of Patent: Feb. 16, 2010

(54) MOBILE RADIOGRAPHY APPARATUS, CONTROL METHOD THEREOF, AND PROGRAM

(75) Inventor: Hirokazu Tanaka, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 721 days.

(21) Appl. No.: 11/408,525

(22) Filed: Apr. 21, 2006

(65) Prior Publication Data

US 2006/0242552 A1    Oct. 26, 2006

(30) Foreign Application Priority Data

Apr. 26, 2005    (JP)    ............... 2005-128622

(51) Int. Cl.
*G06F 15/173* (2006.01)
(52) U.S. Cl. ............... 709/223; 709/217; 709/200
(58) Field of Classification Search ......... 709/223–224, 709/217, 200
See application file for complete search history.

(56) References Cited

U.S. PATENT DOCUMENTS

| 6,359,961 | B1 * | 3/2002 | Aufrichtig et al. | 378/41 |
| 6,702,459 | B2 * | 3/2004 | Barnes et al. | 378/197 |
| 6,760,767 | B1 * | 7/2004 | Miesbauer et al. | 709/223 |
| 6,931,421 | B2 * | 8/2005 | Akagi | 707/203 |
| 7,016,467 | B2 * | 3/2006 | Brooks | 378/102 |
| 7,379,605 | B1 * | 5/2008 | Ticsa | 382/232 |
| 7,434,997 | B2 * | 10/2008 | Koren | 378/204 |
| 7,483,557 | B2 * | 1/2009 | Masuzawa et al. | 382/131 |
| 2004/0190781 | A1 | 9/2004 | Shiibashi et al. | |

FOREIGN PATENT DOCUMENTS

| JP | 2004-041698 | 2/2004 |
| JP | 2004-298266 A | 10/2004 |

OTHER PUBLICATIONS

Okoda Keiji, Japanese Pub. No. 2004-041698.*
Shiibashi Takao, Japanese Pub. No. 2004-298266.*
The above references were cited in a Apr. 25, 2008 Japanese Office Action issued in the counterpart Japanese Patent Application 2005-128622, a which is enclosed.

* cited by examiner

*Primary Examiner*—Philip B Tran
(74) *Attorney, Agent, or Firm*—Cowan, Liebowitz & Latman, P.C.

(57) ABSTRACT

A radiography order information request to request a radiography order information of an information system is transmitted to the information system through a network. Radiography order information corresponding to the radiography order information request is received from the information system through the network. The received radiography order information is stored. Connection to the network is sensed. On the basis of the sensing result, the radiography order information corresponding to the radiography order information request is obtained.

8 Claims, 11 Drawing Sheets

FIG. 4

RADIOGRAPHY ORDER INFORMATION REQUEST  41

| RESERVED AE STATION NAME |
| --- |
| RESERVED PROCEDURE STEP START DATE |
| RESERVED PROCEDURE STEP START TIME |
| MODALITY |
| NAME OF RESERVED DOCTOR |
| NAME OF RESERVED STATION |
| RESERVED PROCEDURE STEP LOCATION |
| RECEIPT NUMBER |
| NAME OF PATIENT |
| PATIENT ID |

RADIOGRAPHY ORDER INFORMATION

| TEST INSTANCE UID |
| --- |
| NAME OF RESERVED DOCTOR |
| CODE VALUE |
| CODE MEANING |
| RECEIPT NUMBER |
| DOCTOR ON ORDER SIDE |
| ORDER DEPARTMENT |
| NAME OF PATIENT |
| PATIENT ID |
| DATE OF BIRTH OF PATIENT |
| SEX OF PATIENT |
| WEIGHT OF PATIENT |
| HEIGHT OF PATIENT |
| AGE OF PATIENT |

FIG. 9

| 61 |
|---|
| RADIOGRAPHY CONDITION NOTIFICATION |
| TEST INSTANCE UID |
| RECEIPT NUMBER |
| NAME OF PATIENT |
| PATIENT ID |
| DATE OF BIRTH OF PATIENT |
| SEX OF PATIENT |
| EXECUTION AE STATION NAME |
| EXECUTION PROCEDURE STEP START DATE |
| EXECUTION PROCEDURE STEP START TIME |
| EXECUTION PROCEDURE STEP CONDITION |
| EXECUTION PROCEDURE STEP END DATE |
| EXECUTION PROCEDURE STEP END TIME |
| CODE VALUE |
| CODE MEANING |
| NAME OF EXECUTION DOCTOR |

MOBILE RADIOGRAPHY APPARATUS, CONTROL METHOD THEREOF, AND PROGRAM

FIELD OF THE INVENTION

The present invention relates to a mobile radiography apparatus which is connected to a network to transmit/receive information to/from an information system which is connected to the network and manages imaging order information, a control method thereof, and a program.

BACKGROUND OF THE INVENTION

Techniques of imaging a transmission intensity distribution of radiation with penetrability, represented by X-rays, have laid foundation for the developments of modern medical technologies. Since the discovery of X-rays, imaging of an X-ray intensity distribution obtained when X-rays pass through an object is done by converting the X-ray intensity distribution into visible light and then forming and developing a latent image on a silver halide film.

Recently, an X-ray image digitizing method using a so-called imaging plate has become popular. In this method, a photostimulable phosphor is used. A latent image that is formed by X-ray irradiation as a stored energy distribution on the photostimulable phosphor is excited by a laser beam, read, and converted into a digital image.

In addition, along with advance in semiconductor technologies, a large-sized solid-state image sensing element, i.e., a so-called flat panel detector having a size of a human body as an object under examination has also been developed. Hence, an X-ray image of an object can be directly digitized without forming a latent image, resulting in efficient diagnosis.

On the other hand, as an information network in a hospital has been built up, information systems for handling information on the network, such as a HIS (Hospital Information System), RIS (Radiology Information System), and PACS (Picture Archiving and Communication System), have been developed while being closely related to the operation of a radiography apparatus.

A hospital information system deals with management information in the hospital in general, including patient information (e.g., a patient ID, patient name, sex, and date of birth) and accounting information. The RIS manages information about imaging by e.g., receiving an imaging order from a clinic and issuing, to the department of radiology, an imaging order containing specific conditions such as the target patient, the part to be imaged, and the imaging equipment to be used for imaging. The RIS also manages imaging conditions by receiving an imaging start/end notification from the imaging order recipient. The PACS executes image data archive management by, e.g., archiving radiographed image data and, upon receiving a past radiographed image data review order, searching for and sending necessary radiographed image data.

Radiography apparatuses in a hospital are classified into stationary types fixed in imaging rooms and mobile types capable of moving in the hospital. A stationary radiography apparatus is connected online to each information system in the hospital. Hence, the apparatus can receive imaging order information from the RIS or transmit an imaging start/end condition to the RIS or a radiographed image to the PACS.

A mobile radiography apparatus can be carried to a hospital facility such as a sickroom, operation room, ICU, or ER to radiograph a patient who cannot come to the imaging room. The apparatus is of a mobile type and normally difficult to connect to a network through a cable. However, for example, patent reference 1 proposes a mobile radiography apparatus wirelessly connectable to a network. In patent reference 1, even the mobile radiography apparatus can access each information system in a hospital, like a stationary type.

[Patent Reference 1] Japanese Patent Laid-Open No. 2004-41698

As described above, a wireless equipment is necessary to make the conventional mobile radiography apparatus access an information system in a hospital.

In the hospital, however, there is a fear of operation errors of medical equipment or influence on patient's cardiac pacemakers. The use of devices that generate radio waves is sometimes limited, and it may be impossible to introduce a wireless equipment. In such an environment, the conventional wireless mobile radiography apparatus is inhibited from accessing the network through a wireless system and is therefore hard to introduce.

SUMMARY OF THE INVENTION

The present invention has been made to solve the above-described problems, and has as its object to provide a mobile radiography apparatus capable of obtaining information about imaging and efficiently appropriately providing the information to an information system without using a wireless system, a control method thereof, and a program.

According to the present invention, the foregoing object is attained providing a mobile radiography apparatus which is connected to a network to transmit/receive information to/from an information system which is connected to the network and manages imaging order information, comprising:

transmitting means for transmitting, to the information system through the network, an imaging order information request to request the imaging order information of the information system;

receiving means for receiving the imaging order information corresponding to the imaging order information request from the information system through the network;

storing means for storing the imaging order information received by the receiving means;

sensing means for sensing connection to the network; and obtaining means for obtaining the imaging order information corresponding to the imaging order information request on the basis of a sensing result of the sensing means.

In a preferred embodiment, the obtaining means obtains the imaging order information corresponding to the imaging order information request from the information system through the network when it is determined as a result of sensing by the sensing means that the mobile radiography apparatus is connected to the network, and obtains, from the storing means, imaging order information already stored in the storing means when it is determined as a result of sensing by the sensing means that the mobile radiography apparatus is not connected to the network.

In a preferred embodiment, the apparatus further comprises:

imaging condition notification means for transmitting, to the information system through the network, an imaging condition notification of imaging by the imaging order information received from the receiving means; and setting means for setting, in the imaging order information, identification information representing that imaging based on the imaging order information stored in the storing means has already been completed.

In a preferred embodiment, when the sensing means detects connection to the network, an imaging start notification and an imaging end notification are transmitted to the information system through the network in correspondence with, of pieces of imaging order information stored in the storing means, imaging order information in which the identification information representing completion of imaging is set.

In a preferred embodiment, the imaging condition notification means transmits, to the information system through the network, imaging start notifications corresponding to all pieces of received imaging order information when the receiving means receives the imaging order information, and when the sensing means detects connection to the network, transmits an imaging end notification to the information system through the network in correspondence with, of pieces of imaging order information stored in the storing means, imaging order information in which the identification information representing completion of imaging is set, and transmits an imaging cancel notification to the information system through the network in correspondence with imaging order information in which the identification information representing completion of imaging is not set.

In a preferred embodiment, the apparatus further comprises time storing means for storing an imaging end time of imaging based on the imaging order information, wherein in transmitting the imaging end notification to the information system through the network, the imaging condition notification means obtains a corresponding imaging end time from the time storing means and sets the imaging end time in the imaging end notification.

In a preferred embodiment, the apparatus further comprises time storing means for storing an imaging start time and an imaging end time of imaging based on the imaging order information, wherein in transmitting the imaging start notification to the information system through the network, the imaging condition notification means obtains a corresponding imaging start time from the time storing means and sets the imaging start time in the imaging start notification, and in transmitting the imaging end notification to the information system through the network, the imaging condition notification means obtains a corresponding imaging end time from the time storing means and sets the imaging end time in the imaging end notification.

According to the present invention, the foregoing object is attained by providing a control method of a mobile radiography apparatus which is connected to a network to transmit/receive information to/from an information system which is connected to the network and manages imaging order information, comprising:

a transmitting step of transmitting, to the information system through the network, an imaging order information request to request the imaging order information of the information system;

a receiving step of receiving the imaging order information corresponding to the imaging order information request from the information system through the network;

a storing step of storing the imaging order information received in the receiving step;

a sensing step of sensing connection to the network; and an obtaining step of obtaining the imaging order information corresponding to the imaging order information request on the basis of a sensing result of the sensing step.

According to the present invention, the foregoing object is attained by providing a program which implements control of a mobile radiography apparatus which is connected to a network to transmit/receive information to/from an information system which is connected to the network and manages imaging order information, comprising:

a program code for a transmitting step of transmitting, to the information system through the network, an imaging order information request to request the imaging order information of the information system;

a program code for a receiving step of receiving the imaging order information corresponding to the imaging order information request from the information system through the network;

a program code for a storing step of storing the imaging order information received in the receiving step;

a program code for a sensing step of sensing connection to the network; and a program code for an obtaining step of obtaining the imaging order information corresponding to the imaging order information request on the basis of a sensing result of the sensing step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 4 is a view showing an example of an imaging order information request according to the first embodiment of the present invention;

FIG. 5 is a view showing an example of imaging order information according to the first embodiment of the present invention;

FIG. 9 is a view showing an example of an imaging condition notification according to the second embodiment of the present invention;

DETAILED DESCRIPTION OF THE PREFERRED EMBODIMENTS

Preferred embodiments of the present invention will now be described in detail in accordance with the accompanying drawings.

In the present invention, a mobile radiography apparatus will be described, which executes imaging on the basis of imaging order information received from an information system in a hospital even in a round of visits in a hospital without a wireless equipment or where the use of a wireless system is inhibited. A mobile radiography apparatus capable of issuing an imaging start/end notification will also be described.

A mobile radiography apparatus capable of adding a correct imaging start/end time in issuing an imaging start/end notification will also be described.

First Embodiment

Figure 1:
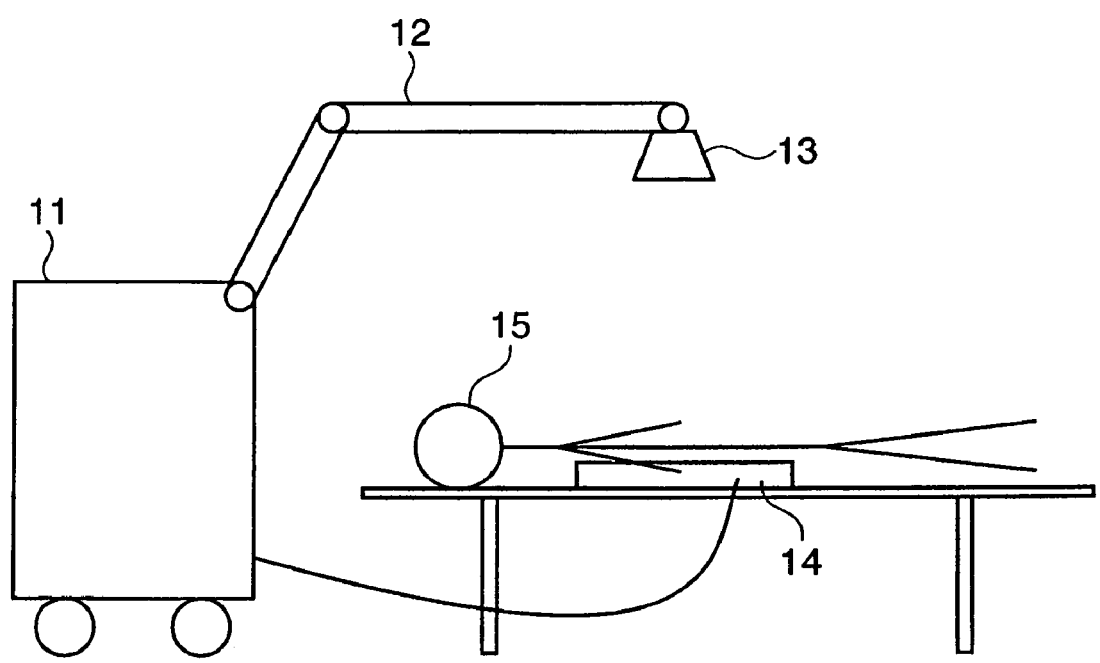
FIG. 1 is a schematic view of a mobile radiography apparatus according to the first embodiment of the present invention.

FIG. 1 is a schematic view of a mobile radiography apparatus according to the first embodiment of the present invention.

A main body 11 of the mobile radiography apparatus (to be referred to as an imaging apparatus hereinafter) has wheels on the bottom and can be moved to a hospital facility such that the sickroom of a patient who cannot come to the imaging room. A mobile arm 12 supporting an X-ray lamp 13 can freely arrange the X-ray lamp 13 at a position suitable for imaging.

An X-ray detection unit 14 obtains digital image data by A/D-converting an analog signal corresponding to the intensity of X-rays that have passed through an object 15 (patient). An example of the X-ray detection unit 14 is a flat panel detector. In imaging, the X-ray detection unit 14 and X-ray lamp 13 are arranged at appropriate positions in accordance with the target imaging part of the object 15. Imaging is executed by X-ray irradiation.

The arrangement of an information system in the hospital will be described next with reference to FIG. 2.

Figure 2:
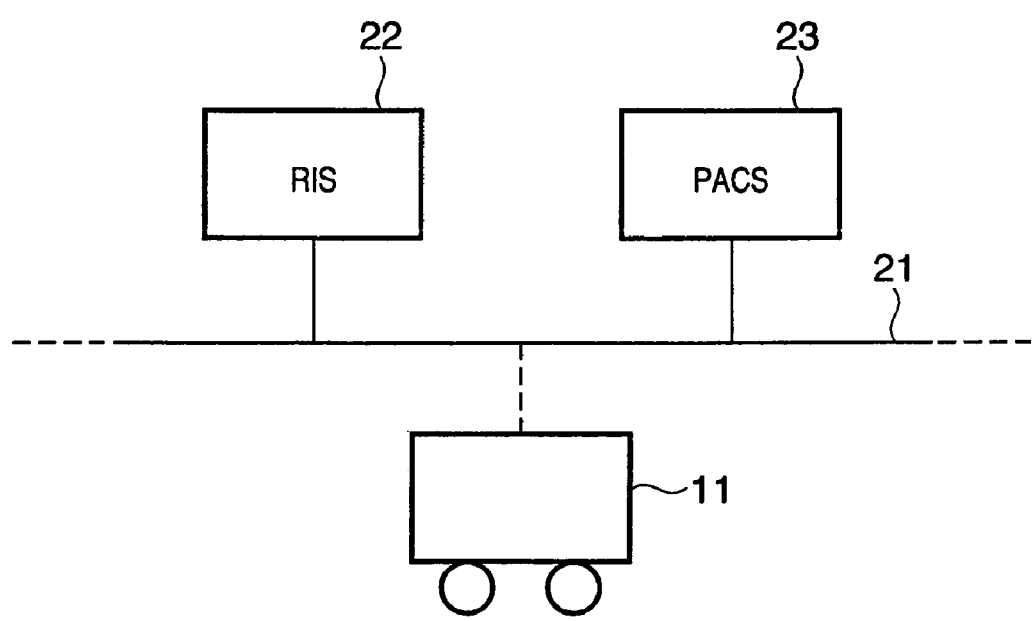
FIG. 2 is a view showing the arrangement of an information system according to the first embodiment of the present invention.

FIG. 2 is a view showing the arrangement of an information system according to the first embodiment of the present invention.

An intra-hospital network 21 is connected to various information devices. The imaging apparatus 11 can be connected to the intra-hospital network 21 through a network cable to exchange information with a RIS 22 or PACS 23.

The intra-hospital network 21 can typically be one of the Internet, LAN, WAN, telephone line, dedicated digital line, ATM, frame relay line, communication satellite channel, cable TV line, and data broadcast radio channel. Alternatively, a so-called communication network implemented by combining them can also be used if it can transmit/receive data.

The RIS 22 is a radiology information system which stores and manages various kinds of information such as radiography order information (to be referred to as imaging order information hereinafter) received from clinics and modality information about various kinds of modalities (e.g., imaging apparatuses) in the hospital. The PACS 23 collects medical images (e.g., radiographed images) from various kinds of modalities connected to the intra-hospital network 21 and stores and manages them.

The imaging apparatus 11 is connected to the intra-hospital network 21 before a round of visits and transmits an imaging order information request to the RIS 22. Upon receiving the imaging order information request, the RIS 22 transmits imaging order information to the imaging apparatus 11. The imaging apparatus 11 stores the received imaging order information in an internal storage medium. During a round of visits, the imaging apparatus 11 is disconnected from the intra-hospital network 21 and moved to the site of imaging to execute imaging. When returning from the round of visits, the imaging apparatus 11 is connected to the intra-hospital network 21 again to transmit radiographed images to the PACS 23.

The RIS 22 and PACS 23 are designed as separate devices. However, they may be designed as one device having both functions.

Each of the various kinds of devices such as the RIS 22 and PACS 23 has standard components provided in a general-purpose computer. Examples of the components are a CPU, RAM, ROM, hard disk, external storage device, network interface, display, keyboard, and mouse.

The internal arrangement of the imaging apparatus 11 will be described next with reference to FIG. 3.

Figure 3:
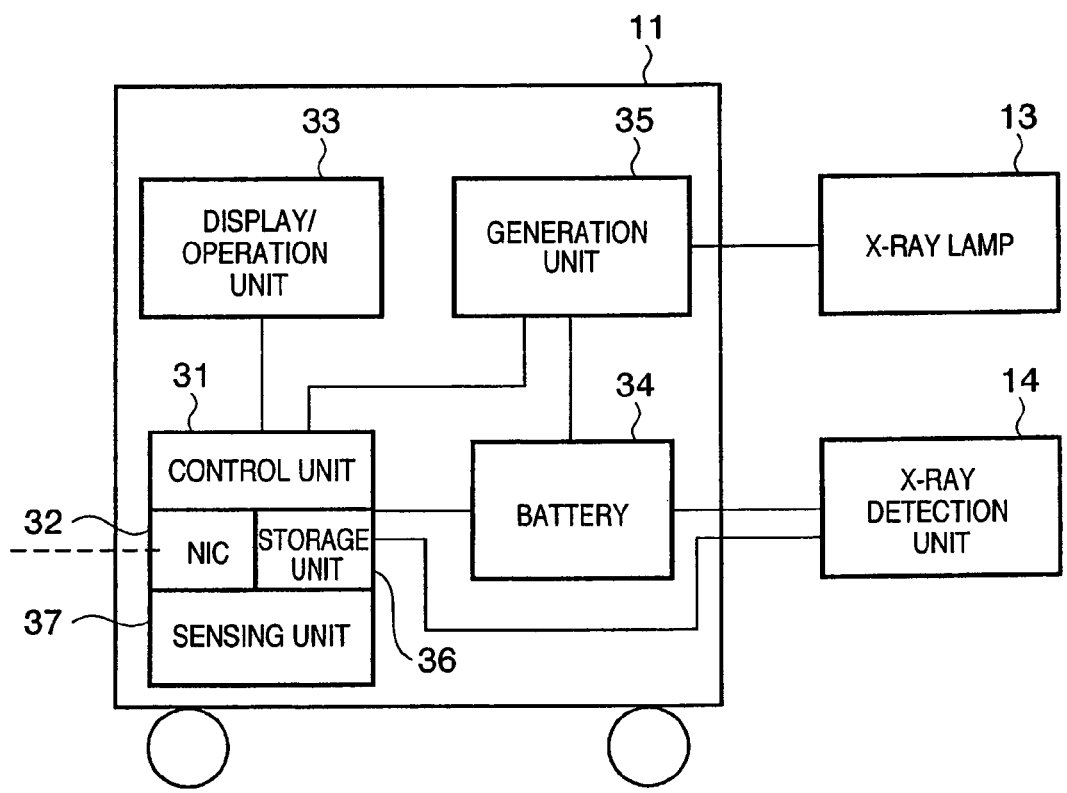
FIG. 3 is a block diagram showing the internal arrangement of the mobile radiography apparatus according to the first embodiment of the present invention.

FIG. 3 is a block diagram showing the internal arrangement of the mobile radiography apparatus according to the first embodiment of the present invention.

A battery 34 is incorporated in the imaging apparatus 11 to supply power to a control unit 31, X-ray detection unit 14, and generation unit 35. The battery 34 is charged in a stand-by state between rounds of visits.

The control unit 31 is connected to the X-ray detection unit 14, generation unit 35, and display/operation unit 33 to control the operation of the entire imaging apparatus 11. The control unit 31 incorporates a NIC (Network Interface Card) 32 so that the imaging apparatus can be connected to the intra-hospital network 21.

The imaging apparatus 11 communicates with the RIS 22 or PACS 23 through the NIC 32. The control unit 31 also includes a storage unit 36 to store imaging order information so that a plurality of pieces of imaging order information received from the RIS 22 can be stored. The control unit 31 also includes a sensing unit 37 to sense network connection.

The display/operation unit 33 includes, e.g., a display with a touch panel, various kinds of keys, and buttons. The display/operation unit 33 serves as a user interface for the operation of the imaging apparatus 11. The display/operation unit 33 displays information for the operator and receives various kinds of inputs from the operator. The control unit 31 controls the generation unit 35 or X-ray detection unit 14 in accordance with input from the display/operation unit 33. The generation unit 35 generates X-rays by appropriately controlling the X-ray lamp 13 in accordance with control information such as a tube voltage, tube current, and irradiation time received from the control unit 31.

An example of an imaging order information request issued from the imaging apparatus 11 to the RIS 22 will be described next with reference to FIG. 4.

FIG. 4 is a view showing an example of an imaging order information request according to the first embodiment of the present invention.

An imaging order information request 41 is information for the RIS 22 to search imaging order information. When the imaging order information request 41 is transmitted to the RIS 22, the RIS 22 searches for imaging order information that matches the search conditions designated by the imaging order information request 41 and transmits the imaging order information to the imaging apparatus 11.

In the imaging order information request 41, "reserved AE station name" is the name of an imaging device. When this name is designated, imaging order information reserved for the imaging device with the name can be searched from the RIS 22. On the basis of "reserved procedure step start date"

and "reserved procedure step start time", imaging order information reserved for a date or time can be searched from the RIS 22.

"Modality" is a value representing a type of imaging apparatus. For example, "DX" representing digital radiography is designated. Since the RIS 22 also handles imaging order information of other imaging apparatuses such as a CT, imaging order information of digital radiography can be searched by designating an appropriate value to "modality".

In addition, "name of reserved doctor", "name of reserved station" (the name of the facility definition of the imaging device), "reserved procedure step location" (a location which is reserved for execution of imaging), "receipt number", "name of patient", and "patient ID" can be designated as search conditions.

An example of imaging order information issued from the RIS 22 to the imaging apparatus 11 will be described next with reference to FIG. 5.

FIG. 5 is a view showing an example of imaging order information according to the first embodiment of the present invention.

Imaging order information 51 is a search result obtained by searching for appropriate imaging order information, on the basis of the imaging order information request 41 transmitted from the imaging apparatus 11, from the imaging order information group stored and managed by the RIS 22. The imaging order information 51 is transmitted to the imaging apparatus 11. Depending on the search conditions designated by the imaging order information request 41, a plurality of imaging order information 51 may be obtained.

The imaging order information 51 contains patent information and information necessary for imaging. "Code value" is the procedure ID (a number to identify an imaging button) of an imaging button arranged on the display/operation unit 33 of the imaging apparatus 11.

The imaging apparatus 11 includes, on the display/operation unit 33, imaging buttons of various irradiation conditions corresponding to the imaging part. Hence, the imaging apparatus 11 can decide, on the basis of the code value contained in the imaging order information 51 received from the RIS 22, the imaging button to be used. When a plurality of imaging processes should be executed for one patient, a plurality of code values are designated. Each code value indicates the name of the imaging part corresponding to the code value.

The imaging order information 51 also contains "test instance UID", "name of reserved doctor", "receipt number", "doctor on order side", and "order department". "Name of patient", "patient ID", "date of birth of patient", "sex of patient", "weight of patient", "height of patient", and "age of patient" are contained as patient information. The patient information is displayed on the display/operation unit 33 and used to identify the patient. The patient information is also added to radiographed images and transmitted from the imaging order information 51 to the PACS 23.

Processing executed by the mobile radiography apparatus 11 according to the first embodiment will be described next with reference to FIG. 6.

Figure 6:
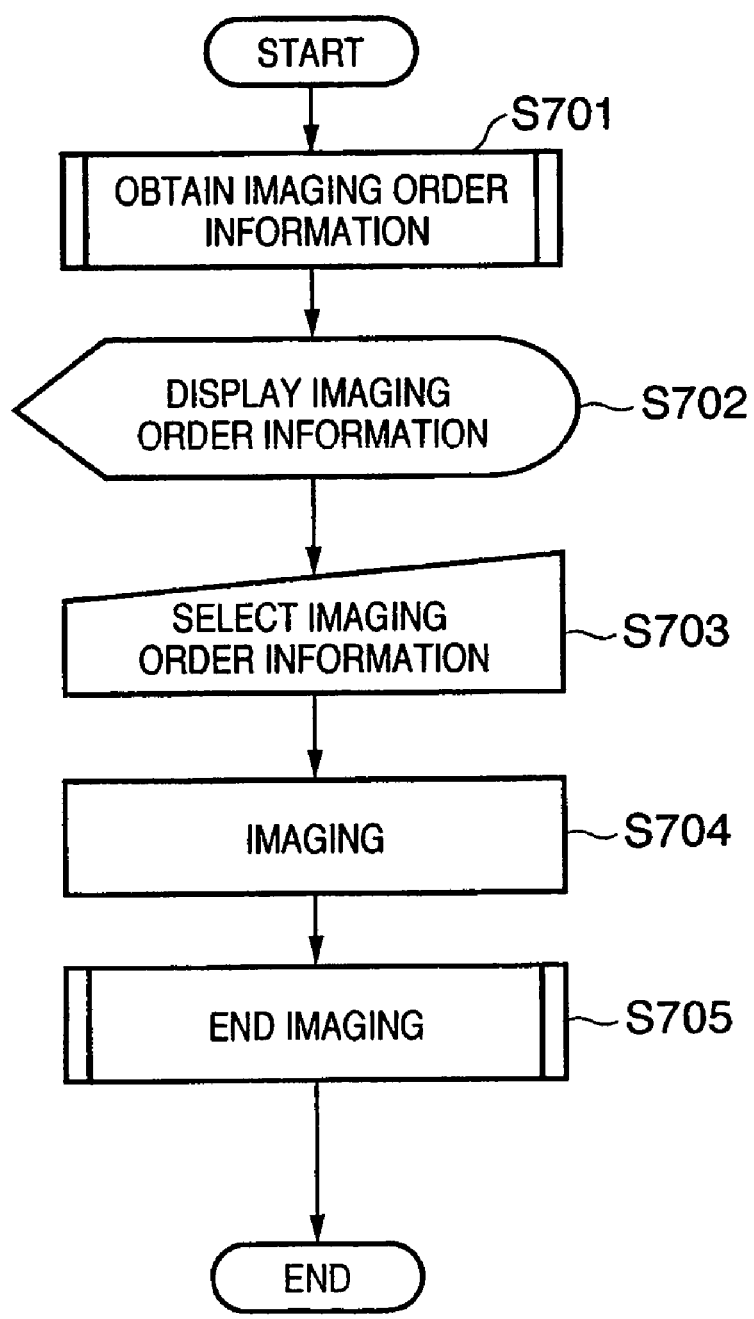
FIG. 6 is a flowchart showing processing executed by the mobile radiography apparatus according to the first embodiment of the present invention.

FIG. 6 is a flowchart showing processing executed by the mobile radiography apparatus according to the first embodiment of the present invention.

The display/operation unit 33 of the imaging apparatus 11 has a test button (not shown) to select a test. The flowchart in FIG. 6 is started by pressing the test button.

In step S701, imaging order information from the RIS 22 is obtained.

Details of the processing in step S701 will be described here with reference to FIG. 7.

Figure 7:
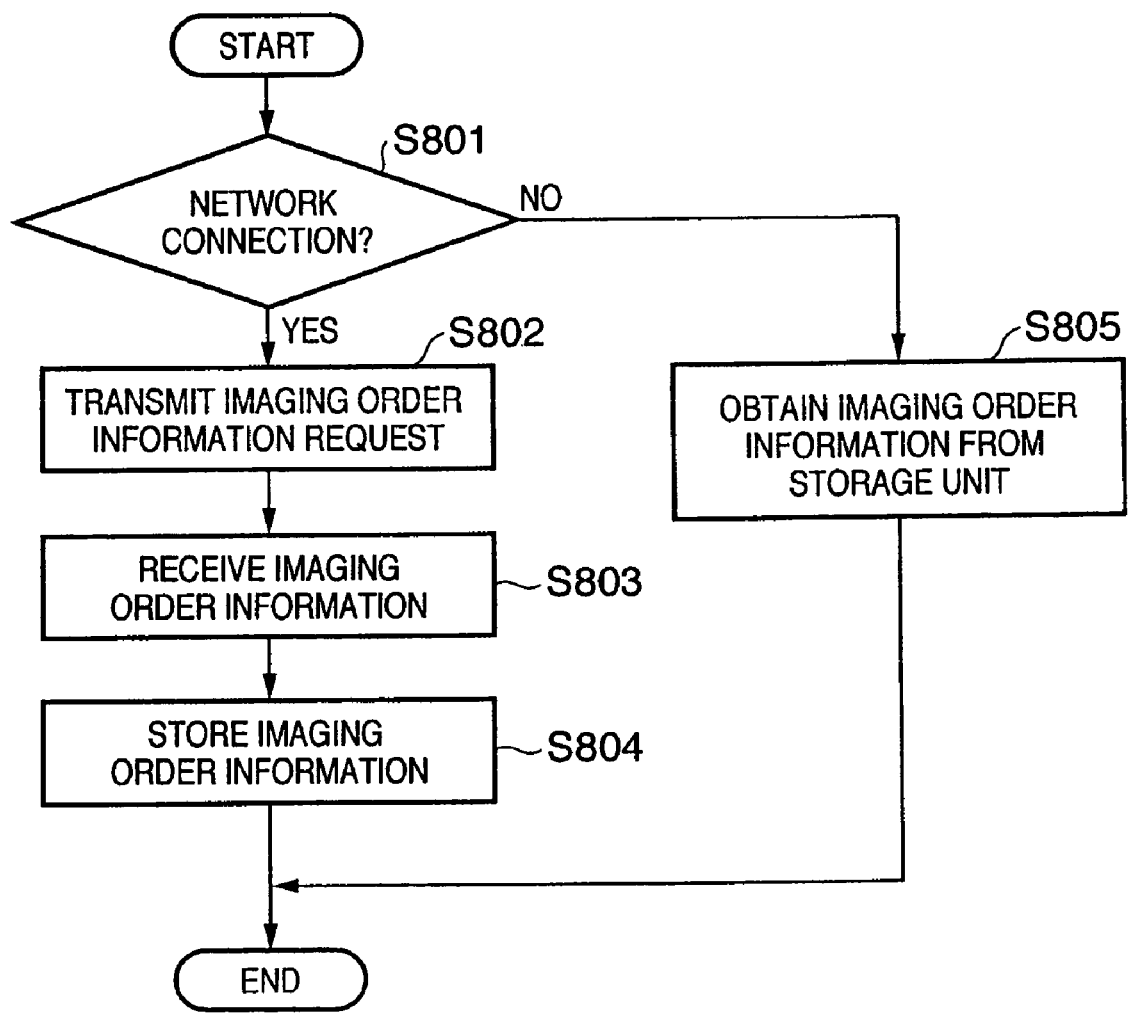
FIG. 7 is a flowchart showing details of processing in step S701 according to the first embodiment of the present invention.

FIG. 7 is a flowchart showing details of processing in step S701 according to the first embodiment of the present invention.

In step S801, it is determined whether the imaging apparatus 11 is connected to the intra-hospital network 21. This determination is done by using the sensing unit 37. If it is determined that the apparatus is connected to the intra-hospital network 21 (YES in step S801), the flow advances to step S802 to transmit the imaging order information request 41 to the RIS 22. The RIS 22 searches for the imaging order information 51 that matches the imaging order information request 41 and transmits the imaging order information 51 to the imaging apparatus 11.

In step S803, the imaging order information 51 transmitted from the RIS 22 is received. In step S804, the received imaging order information 51 is stored in the storage unit 36. The imaging order information 51 is stored in the storage unit 36 together with an additional item of test completion flag (identification information representing that imaging (test) has already been done). The test completion flag is information representing whether imaging has already been executed. If imaging order information is already present in the storage unit 36, the imaging order information is erased, and then, the currently received imaging order information is stored.

If it is determined in step S801 that the apparatus is not connected to the intra-hospital network 21 (NO in step S801), the flow advances to step S805. In step S805, the imaging order information 51 already stored in the storage unit 36 of the control unit 31 (i.e., imaging order information which is received from the RIS 22 during past connection to the intra-hospital network 21) is obtained, and the processing is ended.

FIG. 6 will be described again.

In step S702, a list window of a list of imaging order information 51 is generated and displayed on the display/operation unit 33. In displaying the list window, only pieces of imaging order information 51 without the test completion flag may be displayed.

In step S703, desired imaging order information is selected on the basis of the operator's operation. In step S704, imaging is executed on the basis of the selected imaging order information. When imaging with contents designated by the selected imaging order information is ended, imaging end processing is executed in step S705.

Details of the processing in step S705 will be described here with reference to FIG. 8.

Figure 8:
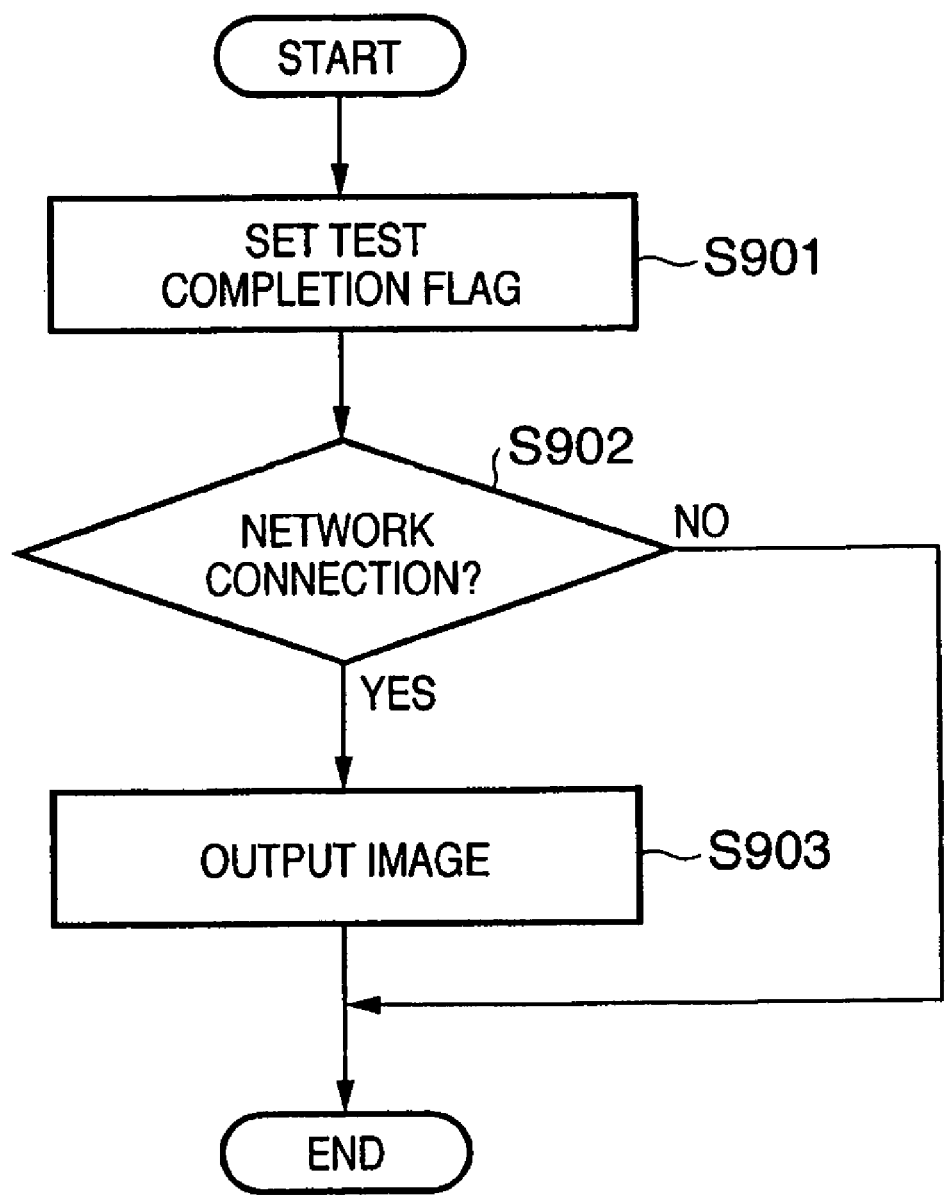
FIG. 8 is a flowchart showing details of processing in step S705 according to the first embodiment of the present invention.

FIG. 8 is a flowchart showing details of processing in step S705 according to the first embodiment of the present invention.

In step S901, the test completion flag is set in the imaging order information 51 in the storage unit 36, which corresponds to imaging that has been executed just now, to store information representing that imaging has been executed. In step S902, it is determined whether the imaging apparatus is connected to the intra-hospital network 21. If it is determined that the apparatus is connected to the intra-hospital network 21 (YES in step S902), the flow advances to step S903. All radiographed images are transmitted to the PACS 23, and the processing is ended.

If it is determined in step S902 that the apparatus is not connected to the intra-hospital network 21 (NO in step S902), the processing is ended.

As described above, according to the first embodiment, before a round of visits, the mobile radiography apparatus obtains the radiography order information 51 from the RIS 22 connected to the intra-hospital network 21 and stores it in the storage unit 36. During the round of visits, the radiography order information is obtained from the storage unit 36. Hence, imaging based on radiography order information obtained from an external information system can be executed even in a hospital where no wireless equipment can be installed.

Second Embodiment

A mobile radiography apparatus used in the second embodiment is the same as in the first embodiment. In the second embodiment, however, an arrangement will be described, which transmits, to a RIS 22, a radiography condition notification (to be referred to as an imaging condition notification hereinafter) such as a radiography start notification or radiography end notification on the basis of various kinds of imaging conditions (the imaging conditions are temporarily stored in a storage unit 36) obtained by imaging by an imaging apparatus 11.

An example of the imaging condition notification will be described with reference to FIG. 9.

FIG. 9 is a view showing an example of the imaging condition notification according to the second embodiment of the present invention.

The executed procedure condition indicated by an imaging condition notification 61 can take three values: "start", "end", and "cancel". Depending on the value, the imaging condition notification 61 becomes a radiography start notification (to be referred to as an imaging start notification), a radiography end notification (to be referred to as an imaging end notification), or a radiography cancel notification (to be referred to as an imaging cancel notification).

"Execution procedure step start date", "execution procedure step start time", "execution procedure step end date", and "execution procedure step end time" indicate the date and time of the start of test and the date and time of the end of test, respectively. "Execution AE station name" is the name of an imaging device that has actually executed imaging. "Name of execution doctor" is the name of the technician who has actually executed imaging. The remaining items are the same as in the imaging order information shown in FIG. 5.

An imaging apparatus which is always connected to an intra-hospital network 21 via a wireless system, as in the prior art, can transmit an imaging start notification to the RIS 22 at the start of test and transmit an imaging end notification or imaging cancel notification to the RIS 22 at the end of test.

The imaging apparatus of the present invention uses no wireless system and is therefore disconnected from the intra-hospital network 21 at both the start and end of test during a round of visits. Hence, the imaging start notification and imaging end notification are transmitted at timings different from the imaging apparatus using a wireless system. The timings will be described below.

Processing from the start to end of imaging is the same as in FIG. 6 of the first embodiment. Details of processing in step S701 are the same as in FIG. 7 of the first embodiment. Details of processing in step S705 are different from the first embodiment and will be described with reference to FIG. 10.

Figure 10:
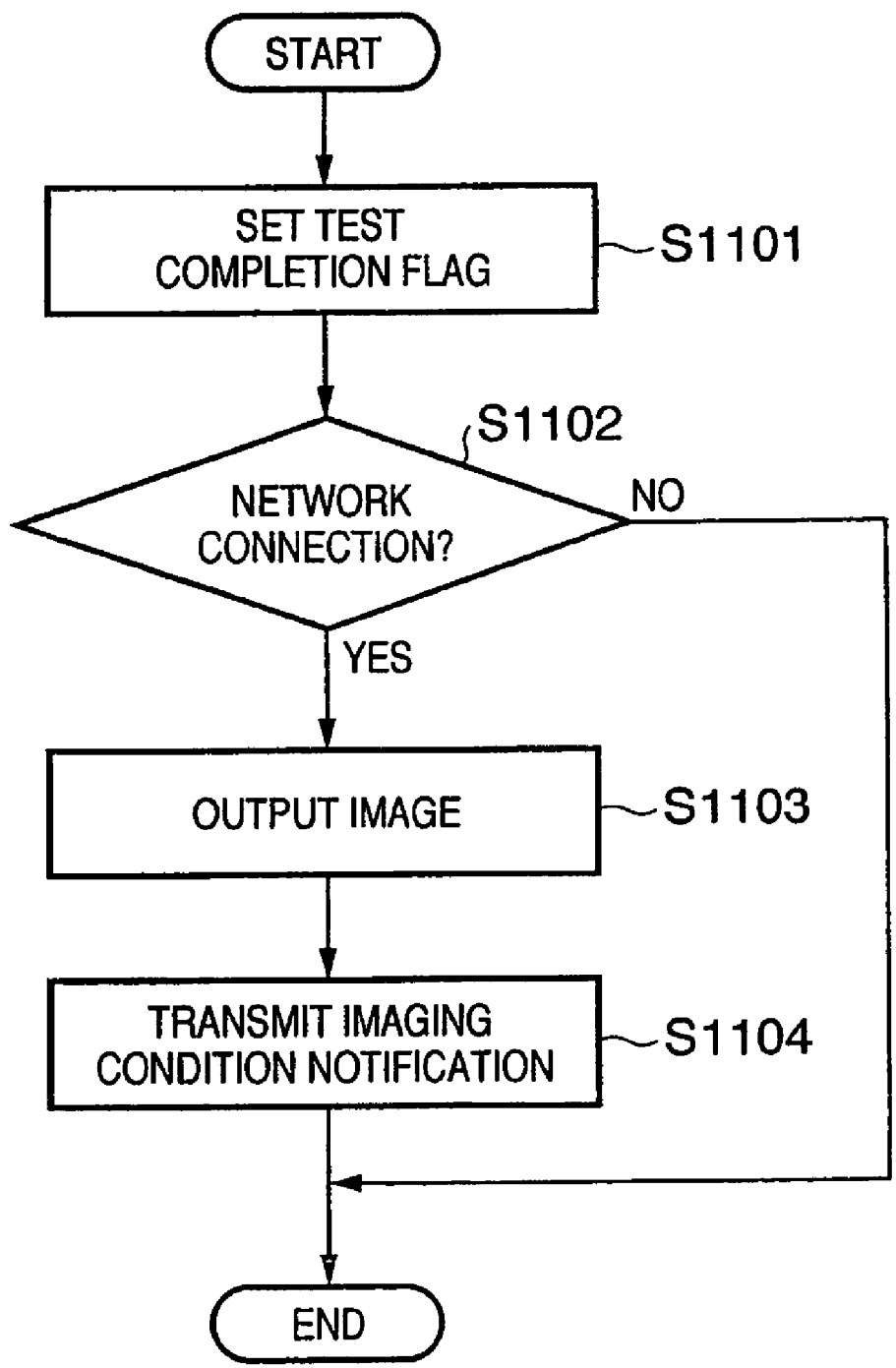
FIG. 10 is a flowchart showing details of processing in step S705 according to the second embodiment of the present invention.

FIG. 10 is a flowchart showing details of processing in step S705 according to the second embodiment of the present invention.

Steps S1101 to S1103 in FIG. 10 correspond to steps S901 to S903 in FIG. 8 of the first embodiment, and a description thereof will be omitted.

In the second embodiment, after the processing in steps S1101 to S1103, the test completion flag of imaging order information stored in the storage unit 36 is referred to in step S1104. In correspondence with imaging order information with the test completion flag being set, an imaging start notification is transmitted to the RIS 22, and an imaging end notification is transmitted to the RIS 22 as an imaging condition notification.

As described above, when the apparatus is connected to the intra-hospital network 21 again, an imaging start notification and imaging end notification are transmitted in association with actually executed imaging. Hence, an imaging condition notification can be implemented without using a wireless system.

As described above, according to the second embodiment, in addition to the effect described in the first embodiment, an imaging condition notification (e.g., an imaging start notification, imaging end notification, and imaging cancel notification) to an external information system can be implemented even in a hospital where no wireless equipment can be installed.

Third Embodiment

A mobile radiography apparatus used in the third embodiment is the same as in the first embodiment. In the third embodiment, however, an arrangement will be described, which transmits a radiography condition notification (to be referred to as an imaging condition notification hereinafter) such as a radiography start notification, radiography end notification, or radiography cancel notification.

An imaging apparatus which is always connected to an intra-hospital network 21 via a wireless system, as in the prior art, can transmit an imaging start notification to a RIS 22 at the start of test and transmit an imaging end notification or imaging cancel notification to the RIS 22 at the end of test.

The imaging apparatus of the present invention uses no wireless system and is therefore disconnected from the intra-hospital network 21 at both the start and end of test during a round of visits. Hence, the imaging start notification, imaging end notification, and imaging cancel notification are transmitted at timings different from the imaging apparatus using a wireless system. The timings will be described below.

The flow from the start to end of imaging is the same as in FIG. 6 of the first embodiment. Details of processing in step S701 are indicated by the flow shown in FIG. 11.

Figure 11:
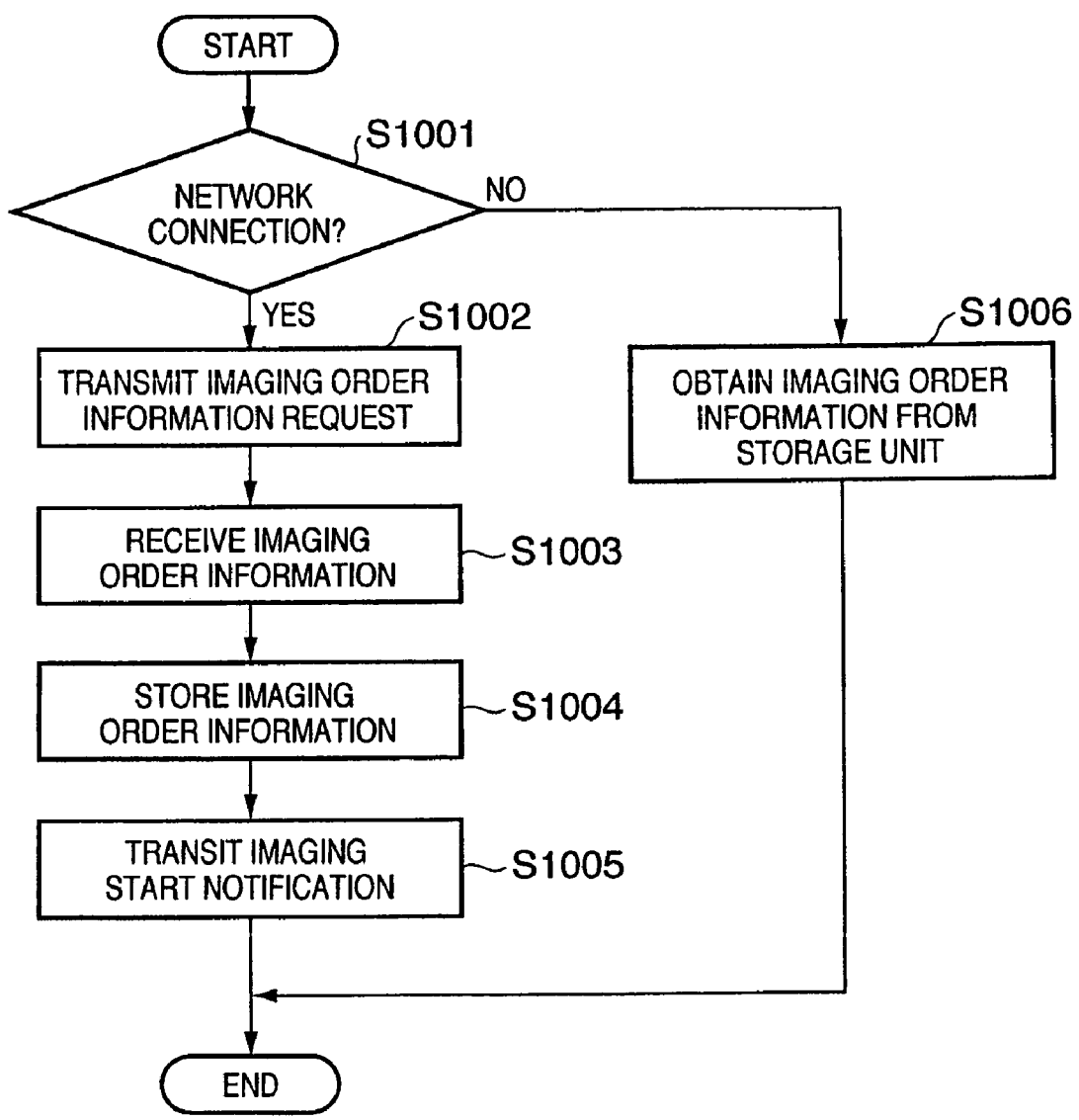
FIG. 11 is a flowchart showing details of processing in step S701 according to the third embodiment of the present invention.

FIG. 11 is a flowchart showing details of processing in step S701 according to the third embodiment of the present invention.

Steps S1001 to S1104 in FIG. 11 correspond to steps S801 to S804 in FIG. 7 of the first embodiment, and a description thereof will be omitted.

In the second embodiment, after the processing in steps S1001 to S1004, imaging start notifications are transmitted to the RIS 22 in correspondence with all pieces of received imaging order information in step S1005.

Upon receiving the pieces of imaging order information, imaging start notifications corresponding to all the pieces of received imaging order information are transmitted to the RIS 22 to notify it of the start of imaging. Hence, no notification need be transmitted at the actual start of imaging.

Details of step S705 of the third embodiment are almost the same as in FIG. 10 of the second embodiment. In the third embodiment, the test completion flag of imaging order information stored in a storage unit 36 is referred to in step S1104. In correspondence with imaging order information with the test completion flag being set, an imaging end notification is transmitted to the RIS 22 as an imaging condition notification. In correspondence with imaging order information without the test completion flag, an imaging cancel notification is transmitted to the RIS 22 as an imaging condition notification.

As described above, according to the third embodiment, upon receiving pieces of imaging order information, imaging start notifications corresponding to all the pieces of received imaging order information are transmitted to the RIS 22. Imaging end notifications and imaging cancel notifications are transmitted at once when the apparatus is connected to the intra-hospital network 21 again. Hence, an imaging condition notification can be implemented without using a wireless system. An imaging condition notification (e.g., an imaging start notification, imaging end notification, and imaging cancel notification) to an external information system can be implemented even in a hospital where no wireless equipment can be installed.

Even in a round of visits by using a plurality of mobile radiography apparatuses, imaging end notifications corresponding to all received imaging orders are transmitted to the RIS 22 in starting the round of visits. The RIS 22 can determine whether imaging is being ordered. Hence, transmission of a duplicate order to another imaging apparatus can be prevented.

Fourth Embodiment

A mobile radiography apparatus used in the fourth embodiment is the same as in the third embodiment and further comprises an arrangement for storing an imaging end time. The imaging end time is stored in, e.g., a storage unit 36.

The flow from the start to end of imaging is the same as in the third embodiment. In the third embodiment, a radiography start notification is transmitted to the RIS 22 in step S1005. At this time, the date and time of transmission are designated to the "execution procedure step start date" and "execution procedure step start time".

However, if a plurality of imaging processes are executed, and the date and time of transmission are designated to "execution procedure step end date" and "execution procedure step end time" of an imaging end notification in step S1104 of FIG. 10, only the imaging end notification of the last imaging process contains the correct date and time.

To prevent this, in step S1101, a test completion flag is set, and simultaneously, the date and time of that point are stored in the storage unit 36 as an imaging end time. In transmitting the imaging end notification in step S1104, the date and time represented by the imaging end time stored in the storage unit 36 are set to "execution procedure step end date" and "execution procedure step end time" of the imaging end notification.

As described above, according to the fourth embodiment, even in an imaging apparatus which uses no wireless system and cannot transmit an imaging end notification in real time, actual imaging end time information can be contained in the imaging end notification to be sent to an external information system.

Fifth Embodiment

A mobile radiography apparatus used in the fifth embodiment is the same as in the second embodiment and further comprises an arrangement for storing an imaging start time and an imaging end time. The imaging start time and imaging end time are stored in, e.g., a storage unit 36.

The flow from the start to end of imaging is the same as in the second embodiment. In the fifth embodiment, if the date and time of transmission are designated in transmitting an imaging start notification and imaging end notification in step S1104, no correct start time and end time are obtained.

In the fifth embodiment, when specific imaging order information is selected in step S703, the date and time of that point are stored in the storage unit 36 as an imaging start time.

Additionally, in step S1101 of FIG. 10, a test completion flag is set, and simultaneously, the date and time of that point are stored in the storage unit 36 as an end time. In transmitting the imaging start notification in step S1104, the imaging start time stored in the storage unit 36 is set to "execution procedure step start date" and "execution procedure step start time". In transmitting the imaging end notification, the imaging end time stored in the storage unit 36 is set to "execution procedure step end date" and "execution procedure step end time".

As described above, according to the fifth embodiment, even in an imaging apparatus which uses no wireless system and cannot transmit an imaging start/end notification in real time, actual imaging start/end time information can be contained in the imaging start/end notification to be sent to an external information system.

As described above, according to the mobile radiography apparatus of the present invention, imaging based on radiography order information obtained from an external information system can be executed even in a hospital where no wireless equipment can be introduced. In addition, an imaging start/end notification can be sent to an external information system.

Hence, the mobile radiography apparatus of the present invention can increase the efficiency of the operation of, e.g., reflecting imaging information on accounting information, like an imaging apparatus that is always connected to a network. In addition, upon detecting network connection, actual imaging start/end time information can be contained in information to be sent to an external information system.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2005-128622, filed Apr. 26, 2005, which is hereby incorporated by reference herein in its entirety.

What is claimed is:

1. A mobile radiography apparatus which is connected to a network to transmit/receive information to/from an information system which is connected to the network via a network cable and manages imaging order information, comprising:
   storing means for storing imaging order information;
   sensing means for sensing connection to the network;
   obtaining means for obtaining imaging order information; and
   X-ray detection means for obtaining digital image data by A/D converting an analog signal corresponding to intensity of X rays irradiated with irradiation condition on the basis of the imaging order information obtained by said obtain means,
   wherein said obtaining means issues imaging order information request to the information system and obtains the imaging order information corresponding to the imaging order information request from the information system through the network cable when it is determined as a result of sensing by said sensing means that the mobile radiography apparatus is connected to the network via the network cable, and
   obtains, from said storing means, imaging order information already stored in said storing means, which corresponds to the imaging order information request when it is determined as a result of sensing by said sensing means that the mobile radiography apparatus is not connected to the network via the network cable.

2. The apparatus according to claim 1, further comprising:
   imaging condition notification means for transmitting, to the information system through the network, an imaging condition notification of imaging by the imaging order information obtained from the information system; and
   setting means for setting, in the imaging order information, identification information representing that imaging based on the imaging order information stored in said storing means has already been completed.

3. The apparatus according to claim 2, wherein when said sensing means detects connection to the network, an imaging start notification and an imaging end notification are transmitted to the information system through the network in correspondence with, of pieces of imaging order information stored in said storing means, imaging order information in which the identification information representing completion of imaging is set.

4. The apparatus according to claim 3, further comprising time storing means for storing an imaging start time and an imaging end time of imaging based on the imaging order information, wherein in transmitting the imaging start notification to the information system through the network, said imaging condition notification means obtains a corresponding imaging start time from said time storing means and sets the imaging start time in the imaging start notification, and in transmitting the imaging end notification to the information system through the network, said imaging condition notification means obtains a corresponding imaging end time from said time storing means and sets the imaging end time in the imaging end notification.

5. The apparatus according to claim 2, wherein said imaging condition notification means
   transmits, to the information system through the network, imaging start notifications corresponding to all pieces of received imaging order information when the imaging order information is received from the information system, and
   when said sensing means detects connection to the network, transmits an imaging end notification to the information system through the network in correspondence with, of pieces of imaging order information stored in said storing means, imaging order information in which the identification information representing completion of imaging is set, and transmits an imaging cancel notification to the information system through the network in correspondence with imaging order information in which the identification information representing completion of imaging is not set.

6. The apparatus according to claim 5, further comprising time storing means for storing an imaging end time of imaging based on the imaging order information, wherein in transmitting the imaging end notification to the information system through the network, said imaging condition notification means obtains a corresponding imaging end time from said time storing means and sets the imaging end time in the imaging end notification.

7. A control method of a mobile radiography apparatus which is connected to a network to transmit/receive information to/from an information system which is connected to the network via a network cable and manages imaging order information, comprising:
   a storing step of storing imaging order information;
   a sensing step of sensing connection to the network; and
   an obtaining step of obtaining imaging order information; and
   an X-ray detection step for obtaining digital image data by A/D converting an analog signal corresponding to intensity of X rays irradiated with irradiation condition on the basis of the imaging order information obtained by said obtaining step, wherein said obtaining step issues imaging order information request to the information system and obtains the imaging order information corresponding to the imaging order information request from the information system through the network cable when it is determined as a result of sensing by said sensing step that the mobile radiography apparatus is connected to the network via the network cable, and obtains, from said storing step, imaging order information already stored in said storing step, which corresponds to the imaging order information request when it is determined as a result of sensing by said sensing step that the mobile radiography apparatus is not connected to the network via the network cable.

8. A program stored on a storage medium readable by a mobile radiography apparatus, the program implementing control of the mobile radiography apparatus which is connected to a network to transmit/receive information to/from an information system which is connected to the network via a network cable and manages imaging order information, comprising:

a program code for a storing step of storing imaging order information;

a program code for a sensing step of sensing connection to the network; and a program code for an obtaining step of obtaining imaging order information; and a program code for an X-ray detection step for obtaining digital image data by A/D converting an analog signal corresponding to intensity of X rays irradiated with irradiation condition on the basis of the imaging order information obtained by said obtaining step, wherein said obtaining step issues imaging order information request to the information system and obtains the imaging order information corresponding to the imaging order information request from the information system through the network cable when it is determined as a result of sensing by said sensing step that the mobile radiography apparatus is connected to the network via the network cable, and obtains, from said storing step, imaging order information already stored in said storing step, which corresponds to the imaging order information request when it is determined as a result of sensing by said sensing step that the mobile radiography apparatus is not connected to the network via the network cable.

* * * * *